(12) United States Patent
Moretti

(10) Patent No.: US 8,178,732 B2
(45) Date of Patent: May 15, 2012

(54) PERFUMING INGREDIENTS IMPARTING SAP AND/OR EARTHY TYPE NOTES

(75) Inventor: Robert Moretti, Grand-Lancy (CH)

(73) Assignee: Firmenich SA, Geneva (CH)

( * ) Notice: Subject to any disclaimer, the term of this patent is extended or adjusted under 35 U.S.C. 154(b) by 169 days.

(21) Appl. No.: 12/808,901

(22) PCT Filed: Jan. 20, 2009

(86) PCT No.: PCT/IB2009/050201
§ 371 (c)(1),
(2), (4) Date: Jun. 17, 2010

(87) PCT Pub. No.: WO2009/093175
PCT Pub. Date: Jul. 30, 2009

(65) Prior Publication Data
US 2010/0291016 A1    Nov. 18, 2010

(30) Foreign Application Priority Data

Jan. 22, 2008 (WO) ............... PCT/IB2008/050223

(51) Int. Cl.
*C07C 35/06* (2006.01)
*C07C 35/17* (2006.01)
*A61K 8/34* (2006.01)
*C11D 3/50* (2006.01)
*C11D 9/44* (2006.01)

(52) U.S. Cl. ........... 568/838; 568/828; 512/23; 510/106
(58) Field of Classification Search .................. None
See application file for complete search history.

(56) References Cited

U.S. PATENT DOCUMENTS 3,857,898 A   12/1974  Schleppnik ............ 568/812
4,631,147 A   12/1986  Matsumoto et al. ....... 512/8
4,719,043 A    1/1988  Schaper et al. ......... 512/8

FOREIGN PATENT DOCUMENTS

EP      0 193 008 B1    9/1986

OTHER PUBLICATIONS

International Search Report and Written Opinion of the International Searching Authority, Application No. PCT/IB2009/050201, mailed May 6, 2009.
Kimura et al., "Nickel-Catalyzed Homoallylation of Aldehydes and Ketones with 1,3-Dienes and Complementary Promotion by Diethylzinc or Triethylborane," Angew. Chem. Int. Ed. 38(3): 397-400 (1999).

*Primary Examiner* — Brian J Davis
(74) *Attorney, Agent, or Firm* — Winston & Strawn LLP

(57) ABSTRACT

The present invention relates to the field of perfumery. More particularly, it concerns specific derivatives of 1-alkenyl cyclopentanol, or 1-alkenyl cyclohexanol, wherein the alkenyle group is branched. These compounds are useful perfuming ingredients capable of imparting sap and/or earthy notes.

10 Claims, No Drawings

PERFUMING INGREDIENTS IMPARTING SAP AND/OR EARTHY TYPE NOTES

This application is a 371 filing of International Patent Application PCT/IB2009/050201 filed Jan. 20, 2009.

TECHNICAL FIELD

The present invention relates to the field of perfumery. More particularly, it concerns specific derivatives of 1-alkenyl cyclopentanol, or 1-alkenyl cyclohexanol, wherein the alkenyle group is branched. These compounds are useful perfuming ingredients.

The present invention concerns the use of said compounds in the perfumery industry as well as the compositions or articles containing said compound.

PRIOR ART

To the best of our knowledge, none of the invention's compounds has been reported in the context of the perfumery art. In general the known compounds were reported in synthetic publication as simple intermediates or products of a specific methodology.

Many compounds are even new compounds.

The closest prior art is U.S. Pat. No. 3,857,898, which reports the use of 1-(3'hexenyl)-1-cyclopentanol or cyclohexanol as perfuming ingredients capable of imparting green, floral, rosy notes. The prior art compounds, when compared to the present ones, differ significantly by having a linear substituent on the cycloalkanol group, and by moreover possessing quite different organoleptic properties.

Therefore, this prior art document does not report or suggest any usefulness of the present compounds in the field of perfumery.

DESCRIPTION OF THE INVENTION

We have now surprisingly discovered that a compound of formula

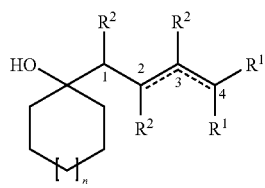

(I)

wherein n represents 0 or 1, a dotted line represents a double bond and the other a single bond;

each $R^1$, independently from each other, represents a hydrogen atom or a methyl or ethyl group; and at least one $R^2$ group is a methyl or ethyl group and the others are a hydrogen atom or a methyl or ethyl group;

can be used as perfuming ingredient, for instance to impart odor notes of the sap and/or earthy type.

According to a particular embodiment of the invention, said compounds (I) are to those wherein n is 0.

According to a particular embodiment of the invention, said compounds (I) are of formula

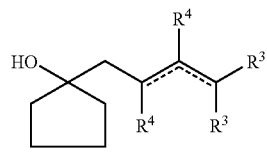

(II)

wherein a dotted line represents a double bond and the other a single bond;

each $R^3$, independently from each other, represents a hydrogen atom or a methyl or ethyl group; and one $R^4$ group is a methyl or ethyl group and the other $R^4$ group is a hydrogen atom, or a methyl or ethyl group.

According to any one of the above-mentioned embodiments, the compounds of formula (I) or (II) are those of the formulae

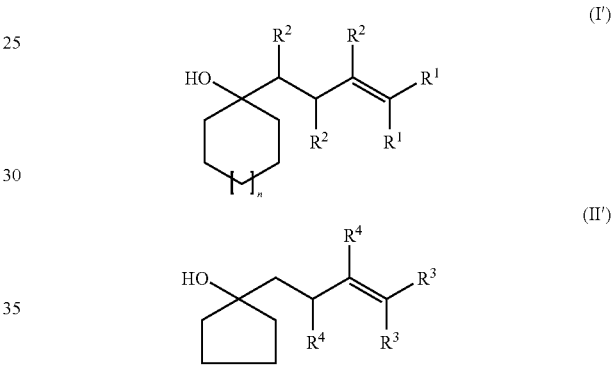

or wherein n and $R^1$ to $R^4$ have the meaning provided above.

The compounds of formula (I) all possess a carbon-carbon double bond, and therefore can be in the form of isomers of configuration E or Z, or of a mixture thereof. Furthermore, said compounds (I) can be also optically active or in a racemic form.

Said compounds of formula (I') wherein n is 0, as well as the compounds of formula II'), are new compounds and therefore are an aspect of the present invention.

According to any one of the above embodiments, in the formulae (I) or (I') particularly suitable compounds can be those wherein at least one $R^2$ group is methyl or to ethyl group and at least one $R^2$ group is a hydrogen atom.

According to any one of the above embodiments, in the formulae (I), (II), (I') or (II'), particularly suitable compounds can be those wherein said $R^2$ or $R^4$, when they are not hydrogen atom, represent a methyl group.

According to any one of the above embodiments, in the formulae (I), (II), (I') or (II'), particularly suitable compounds can be those wherein one $R^1$ or $R^3$ is a hydrogen atom and the other a methyl group.

In particular, a specific object of the present invention is 1-[2-methyl-3-pentenyl]-cyclopentanol, in the form of an isomer of configuration E or Z or of a mixture thereof.

As typical examples of the invention's compounds, one may cite 1-[(3E)-2-methyl-3-pentenyl]-cyclopentanol which possesses an odor characterized by sap, umbellifer, nettle notes. The odor of this compound is remarkably natural and reminds of the odor of hazelnut leave or of freshly cut hazelnut wood.

This compound is very much appreciated due to its capability to combine with truthfulness the freshness of the sap note and the strength of the humus, earthy aspect of nettle or umbellifer.

When the odor of 1-[(3E)-2-methyl-3-pentenyl]-cyclopentanol is compared with the one of 1-(3'hexenyl)-1-cyclopentanol, disclosed in the above-mentioned prior art document, then the invention's compound distinguishes itself by having a totally different odor (i.e. the one described above) and by lacking completely floral, rosy note of the prior art compound.

As other examples of invention's compound one may also cite the following ones: 1-(2,3-dimethyl-3-butenyl)cyclopentanol; odor: earthy and minty notes; 1-(2-methyl-3-butenyl)cyclopentanol; odor: earthly/cellar, camphoreceous; 1-(2-methyl-2-pentenyl)cyclopentanol; odor: pyrazine, carrot, earthy, beet 1-[(3E)-2-methyl-3-pentenyl]-cyclohexanol; odor: pyrazine, earthy geonol, rooty, cellar; 1-(2,3-dimethyl-3-butenyl)cyclohexanol; odor: camphoreceous, earthy; 1-(2-methyl-3-butenyl)cyclohexanol; odor: earthly, carrot.

As mentioned above, the invention concerns the use of a compound of formula (I) as perfuming ingredient. In other words it concerns a method to confer, enhance, improve or modify the odor properties of a perfuming composition or of a perfumed article, which method comprises adding to said composition or article an effective amount of at least a to compound of formula (I). By "use of a compound of formula (I)" it has to be understood here also the use of any composition containing compound (I) and which can be advantageously employed in perfumery industry as active ingredients.

Said compositions, which in fact can be advantageously employed as perfuming ingredient, are also an object of the present invention.

Therefore, another object of the present invention is a perfuming composition comprising:
i) as perfuming ingredient, at least one invention's compound as defined above;
ii) at least one ingredient selected from the group consisting of a perfumery carrier and a perfumery base; and
iii) optionally at least one perfumery adjuvant.

By "perfumery carrier" we mean here a material which is practically neutral from a perfumery point of view, i.e. that does not significantly alter the organoleptic properties of perfuming ingredients. Said carrier may be a liquid or a solid.

As liquid carrier one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as dipropyleneglycol, diethyl phthalate, isopropyl myristate, benzyl benzoate, 2-(2-ethoxyethoxy)-1-ethanol or ethyl citrate, which are the most commonly used.

As solid carrier one may cite, as non-limiting examples, absorbing gums or polymers, or yet encapsulating materials. Examples of such materials may comprise wall-forming and plasticizing materials, such as mono, di- or trisaccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- und Gehermittel in Lebensmittel, Band 2 der Schriftenreihe Lebensmittelchemie, Lebensmittelqualität, Behr's VerlagGmbH & Co., Hamburg, 1996. The encapsulation is a well known process to a person skilled in the art and may be performed, for instance, by using techniques such as spray-drying, agglomeration or yet extrusion; or consists of a coating encapsulation, including coacervation and complex coacervation techniques.

By "perfumery base" we mean here a composition comprising at least one perfuming co-ingredient.

Said perfuming co-ingredient is not of the formula (I). Moreover, by "perfuming co-ingredient" it is meant here a compound which is used in perfuming preparation or composition to impart a hedonic effect. In other words such a co-ingredient, to be considered as being a perfuming one, must be recognized by a person skilled in the art as being able to impart or modify in a positive or pleasant way the odor of a composition, and not just as having an odor.

The nature and type of the perfuming co-ingredients present in the base do not warrant a more detailed description here, which in any case would not be exhaustive, the skilled person being able to select them on the basis of its general knowledge and according to intended use or application and the desired organoleptic effect. In general terms, these perfuming co-ingredients belong to chemical classes as varied as alcohols, aldehydes, ketones, esters, ethers, acetates, nitriles, terpenoids, nitrogenous or sulphurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

By "perfumery adjuvant" we mean here an ingredient capable of imparting additional added benefit such as a color, a particular light resistance, chemical stability, etc. A detailed description of the nature and type of adjuvant commonly used in perfuming bases cannot be exhaustive, but it has to be mentioned that said ingredients are well known to a person skilled in the art.

An invention's composition consisting of at least one compound of formula (I) and at least one perfumery carrier represents a particular embodiment of the invention as well as a perfuming composition comprising at least one compound of formula (I), at least one perfumery carrier, at least one perfumery base, and optionally at least one perfumery to adjuvant.

It is useful to mention here that the possibility to have, in the compositions mentioned above, more than one compound of formula (I) is important as it enables the perfumer to prepare accords, perfumes, possessing the odor tonality of various compounds of the invention, creating thus new tools for their work.

Preferably, any mixture resulting directly from a chemical synthesis, e.g. without an adequate purification, in which the compound of the invention would be involved as a starting, intermediate or end-product could not be considered as a perfuming composition according to the invention.

Furthermore, the invention's compound can also be advantageously used in all the fields of modern perfumery to positively impart or modify the odor of a consumer product into which said compound (I) is added. Consequently, a perfumed article comprising:

i) as perfuming ingredient, at least one compound of formula (I), as defined above, or an invention's perfuming composition; and
ii) a consumer product base;
is also an object of the present invention.

For the sake of clarity, it has to be mentioned that, by "consumer product base" we mean here a consumer product, which is compatible with perfuming ingredients. In other words, a perfumed article according to the invention comprises the functional formulation, as well as optionally additional benefit agents, corresponding to a consumer product, e.g. a detergent or an air freshener, and an olfactive effective amount of at least one invention's compound.

The nature and type of the constituents of the consumer product do not warrant a more detailed description here, which in any case would not be exhaustive, the skilled person being able to select them on the basis of its general knowledge and according to the nature and the desired effect of said product.

Examples of suitable consumer product bases include solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or anti-perspirants, air fresheners and also cosmetic preparations. As detergents to there are intended applications such as detergent compositions or cleaning products for washing up or for cleaning various surfaces, e.g. intended for textile, dish or hard-surface treatment, whether they are intended for domestic or industrial use. Other perfumed articles are fabric refreshers, ironing waters, papers, wipes or bleaches.

Some of the above-mentioned consumer product bases may represent an aggressive medium for the invention's compound, so that it may be necessary to protect the latter from premature decomposition, for example by encapsulation.

The proportions in which the compounds according to the invention can be incorporated into the various aforementioned articles or compositions vary within a wide range of values. These values are dependent on the nature of the article to be perfumed and on the desired organoleptic effect as well as the nature of the co-ingredients in a given base when the compounds according to the invention are mixed with perfuming co-ingredients, solvents or additives commonly used in the art.

For example, in the case of perfuming compositions, typical concentrations are in the order of 0.01% to 30% by weight, or even more, of the compounds of the invention based on the weight of the composition into which they are incorporated. Concentrations lower than these, such as in the order of 0.001% to 10% by weight, can be used when these compounds are incorporated into perfumed articles, percentage being relative to the weight of the article.

The invention's compounds can be prepared according to a method as described in the examples. For example, it can be used a nickel catalysed coupling of a suitable diene with a suitable ketone (e.g. see Masanari Kimura et al. in *Angew. Chem. Int. Ed*, 1999, 38, pg 397), or an addition of an organometallic compound (e.g. a Grignard) on a suitable unsaturated ester or ketone (see the examples).

EXAMPLES

The invention will now be described in further detail by way of the following examples, wherein the abbreviations have the usual meaning in the art, the temperatures are indicated in degrees centigrade (° C.); the NMR spectral data were recorded in $CDCl_3$ (if not stated otherwise) with a 360 or 400 MHz machine for $^1H$ and $^{13}C$, the chemical displacements δ are indicated in ppm with respect to TMS as standard, the coupling constants J are expressed in Hz.

Example 1

Synthesis of Compounds of Formula (I) by a Nickel Catalyzed Coupling

General Procedure:
Diethylzinc (1 molar solution in hexanes; 1.5 eq.) is added over a 1 hour to a pre-cooled (−78° C.) suspension of Ni(acac)$_2$ (0.1 eq.), ketone (1.0 eq.) and diene (4 eq.) in dry THF (2-3 ml/mmol ketone) under nitrogen. The cooling bath is then removed and the reaction is stirred overnight. It is next cooled to 0° C. before adding (slowly at the beginning!) 5% aqueous HCl (1 ml/mmol ketone) to it. The reaction is extracted twice with ether. Each organic fraction is washed with 5% aqueous HCl and brine. Combined organic fractions are dried over anhydrous solid sodium sulfate. The solvent is removed under vacuum and the product is isolated by column chromatogramphy on silicagel (eluent=heptane/EtOAc 19:1) followed by bulb-to-bulb distillation.

1-[(3E)-2-Methyl-3-Pentenyl]Cyclopentanol

Prepared according to the general procedure, with the following quantities:
Cyclopentanone (20.02 g, 0.238 mol)
Methylpentadiene (70% chemical purity, 111.6 g, 0.95 mol)
Ni(acac)$_2$ (6.11 g, 0.024 mol)
Diethylzinc (1 molar in hexanes, 360 ml, 0.36 mol)
THF (400 ml)
The title compound is obtained in 41% yield, as mixture of isomers (80/3/3/13).
B.P.=87-89° C./8.0 mbar
$^1$H-NMR: 0.95-1.03 (m, 3H); 1.40-1.85 (m, 13H); 1.90-2.08 (m, 1H); 2.27-2.47 (m, 1 H); 5.40-5.53 (m, 2H).

1-[(3E)-2-Methyl-3-Pentenyl]Cyclohexanol

Prepared according to the general procedure, with the following quantities:
Cyclohexanone (10.0 g, 0.102 mol)
Methylpentadiene (70%, 47.83 g, 0.408 mol)
Ni(acac)$_2$ (2.62 g, 0.01 mol))
Diethylzinc (1 molar in hexanes, 153 ml, 0.153 mol)
THF (300 ml)
The title compound is obtained in 51% yield.
B.P.=100° C./3 mbar
$^1$H-NMR: 0.98 (d, J=7 Hz, 3H); 1.20-1.35 (m, 2H); 1.37-1.68 (m, 13H); 1.87 (broad s, 1H); 2.37-2.49 (m, 1H); 5.36-5.53 (m, 2H).

1-(2,3-Dimethyl-3-Butenyl)Cyclopentanol

Prepared according to the general procedure, with the following quantities:
Cyclopentanone (10.01 g, 0.119 mol)
Dimethylbutadiene (39.1 g, 0.476 mol)
Ni(acac)$_2$ (3.06 g, g, 0.012 mol)
Diethylzinc (1 molar in hexanes, 180 ml, 0.18 mol)
THF (300 ml)
The title compound is obtained in 38% yield, as a mixture of isomers (67/8/19).
B.P.=100° C./5 mbar $^1$H-NMR: 1.04 (d, J=7 Hz, 3H); 1.40-1.95 (m, 13H); 2.25-2.82 (m, 2H); 4.72-5.02 (m, 2H).

1-(2,3-Dimethyl-3-Butenyl)Cyclohexanol

Prepared according to the general procedure, with the following quantities:
Cyclohexanone (10.0 g, 0.102 mol)
Dimethylbutadiene (47.8 g, 0.408 mol)
Ni(acac)$_2$ (2.62 g, 0.01 mol))
Diethylzinc (1 molar in hexanes, 153 ml, 0.153 mol)
THF (300 ml)
The title compound is obtained in 38% yield as a 82:18 mixture of isomers.
B.P.=100° C./1 mbar
$^1$H-NMR: 1.02 (d, J=7, 3H); 1.20-1.85 (m, 16H); 2.52-2.62 (m, 1H); 4.72 (m, 1H); 4.83 (m, 1H).

1-(2-Methyl-3-Butenyl)Cyclohexanol

Prepared according to the general procedure, with the following quantities:
Cyclohexanone (10.0 g, 0.102 mol)
Isoprene (27.76 g, 0.408 mol)
Ni(acac)$_2$ (2.62 g, 0.01 mol))
Diethylzinc (1 molar in hexanes, 153 ml, 0.153 mol)
THF (300 ml)
The title product is obtained in 72% yield.
B.P.=100° C./5 mbar
$^1$H-NMR: 1.02 (d, J=7, 3H); 1.20-1.80 (m, 13H); 2.42-2.54 (m, 1H); 4.92-5.10 (m, 2 H); 5.77-5.88 (m, 1H).

Example 2

Synthesis of Compounds of Formula (I) by Addition of an Organometallic Compound on a Ketone or Ester 1-(3,4-Dimethyl-3-Pentenyl)Cyclopentanol Magnesium turnings (9.53 g, 0.39 mol) were covered with dry diethyl ether (50 ml) at room temperature under nitrogen. 1,2-Dibromoethane (0.5 ml) was added in one portion. As soon as a visible reaction had started (bubbling), magnetic stirring was switched on and a solution of 1,4-dibromobutane (50 g, 0.225 mol) in dry diethyl ether (360 ml) was added at a rate such as to maintain a constant reflux (1 hour). The reaction was further refluxed for 1 hour before cooling in an ice-water bath. Ethyl 4,5-dimethyl-4-hexenoate (26.5 g, 0.156 mol) in dry diethyl ether (30 ml) was added dropwise. Then the reaction was warmed up to room temperature and the reaction was refluxed for 1 hour. It was recooled in an ice-water bath before adding a saturated aqueous ammonium chloride solution (250 ml, slowly). After warming up to room temperature and shaking vigorously, the phases were separated. The organic phase was washed with aqueous saturated bicarbonate (250 ml) and water (500 ml). Each aqueous phase was re-extracted with diethyl ether (250 ml). Combined extracts were dried over anhydrous sodium sulfate. The product was purified by column chromatography on silica gel (eluting with heptanes/ethyl acetate 11:1 to 3:1) followed by bulb-to-bulb distillation (110° C./1 mbar). 22.62 g of the title compound (99.6% pure, 0.122 mol, 78%) were obtained.

$^{13}$C-NMR: 127.81 (s), 124.01 (s), 82.68 (s), 39.72 (t), 39.62 (t), 29.76 (t), 23.92 (t), 20.59 (q), 20.03 (q), 18.35 (q).
$^1$H-NMR: 2.18-2.11 (m, 2H), 1.88-1.75 (m, 2H), 1.68-1.55 (m, 17 h); 1.50 (s, 1H).

(E)-1-(2-Methylhex-3-Enyl)Cyclopentanol

The same procedure as for 1-(3,4-dimethyl-3-pentenyl)cyclopentanol was used, with the following quantities:
Magnesium: 1.48 g (0.061 mol)-1,4-Dibromobutane: 7.55 g (0.035 mol)-Ethyl 3-methyl-4-heptenoate: 3.93 g (0.023 mol).
The product was purified by column chromatography on silica gel (heptanes/ethyl acetate 5:1) followed by bulb-to-bulb distillation (90° C./1 mbar). 3.14 g (0.017 mol, 75%) of pure, desired, compound were obtained.
$^{13}$C-NMR: 136.86 (d), 131.36 (d), 82.98 (s), 48.47 (t), 40.98 (t), 39.97 (t), 35.02 (d), 25.45 (t), 23.74 (t), 23.71 (t), 23.22 (q), 13.71 (q).
$^1$H-NMR: 5.58-5.52 (m, 1H), 5.45-5.37 (m, 1H), 2.48-2.36 (m, 1H), 2.05-1.95 (m, 4H), 1.83-1.40 (m, 9H), 1.00 (d, J=7, 3H), 0.96 (t, J=7, 3H).

Example 3

Preparation of a Perfuming Composition

A perfuming base, of the peach type, was prepared by admixing the following ingredients:

| Ingredient | Parts by weight |
|---|---|
| Ethyl acetate | 390 |
| Ethyl acetoacetate | 60 |
| Benzoic Aldehyde | 10 |
| Allyl caproate | 35 |
| Cis-Jasmone | 10 |
| 10%* Damascenone[1] | 10 |
| 4-Decanolide | 90 |
| Delta Decalactone | 25 |
| Dodecalactone | 20 |
| Delta Dodecalactone | 20 |
| Linalol | 150 |
| Linalyl oxide | 85 |
| Phenethylol | 35 |
| Benzyl salicylate | 160 |
| 1%* (1R,4R)-8-mercapto-3-p-menthanone | 10 |
| Gamma Undecalactone | 45 |
| 4-Pentanolide | 25 |
| 10%* Violet essential oil | 20 |
| | 1200 |

*in dipropyleneglycol
[1] (E)-1-(2,6,6-trimethyl-1,3-cyclohexadien-1-yl)-2-buten-1-one; origin: Firmenich SA, Switzerland The addition of 30 parts by weight of 1-[(3E)-2-methyl-3-pentenyl]-cyclopentanol to the above-described perfuming composition imparted to the peach odor, note of the original perfuming composition, a sap salivating aspect, slightly bitter and very natural and decreased the sulfury-lactonic aspect of the original composition. This effect was not observed when instead of the invention's compound it was added the same amount of 1-(3'hexenyl)-1-cyclopentanol, indeed in this case it was obtained a rather disturbing fragrance where the prior art compound did not impart a tangible positive modification but rather conferred to the original peach/lactonic notes a disturbing floral rosy character.

Example 4

Preparation of a Perfuming Composition

A perfuming base, of the green tea type, was prepared by admixing the following ingredients:

| Ingredient | Parts by weight |
| --- | --- |
| Styrallyl acetate | 10 |
| Hexylcinnamic aldehyde | 100 |
| Hexyl caproate | 20 |
| Cis-Jasmone | 5 |
| 4-Cyclohexyl-2-methyl-2-butanol | 90 |
| Cis-2-pentyl-1-cyclopentanol | 130 |
| 10%* Damascenone[1)] | 20 |
| 4-Decanolide | 20 |
| Delta decalactone | 5 |
| 10%* Gamma hexalactone | 10 |
| Geraniol | 60 |
| Geranyl Acetone | 15 |
| Hedione ®[2)] | 340 |
| Hexyl isobutyrate | 30 |
| Linalol | 350 |
| Mate essential oil | 15 |
| 10%* Oxane[3)] | 5 |
| 1%* (2E,6Z)-2,6-nonadienal | 20 |
| Phenethylol | 150 |
| 5-Methyl-exo-tricyclo[6.2.1.0(2,7)]undecan-4-one | 5 |
| Terpenes ex orange | 200 |
| Ionone alpha | 30 |
| Ionone beta | 70 |
| | 1700 |

*in dipropyleneglycol
[1)](E)-1-(2,6,6-trimethyl-1,3-cyclohexadien-1-yl)-2-buten-1-one; origin: Firmenich SA, Switzerland
[2)]Methyl dihydrojasmonate; origin: Firmenich SA, Switzerland
[3)]Cis-2-methyl-4-propyl-1,3-oxathiane; origin: Firmenich SA, Switzerland The addition of 50 parts by weight of 1-[(3E)-2-methyl-3-pentenyl]-cyclopentanol to the above-described perfuming composition imparted a clear leave/sap connotation redirecting to overall fragrance towards a "green tea leave" type. Once again the olfactive effect obtained using the prior art compound I-(3'hexenyl)-1-cyclopentanol was totally devoid of such pleasant effect.

Example 5

Preparation of a Perfuming Composition

A perfuming base, of the woody type, was prepared by admixing the following ingredients:

| Ingredient | Parts by weight |
| --- | --- |
| Cedar wood essential oil | 500 |
| Celeri essential oil | 100 |
| Helvetolide ®[1)] | 100 |
| Trans-1-(2,2,6-trimethyl-1-cyclohexyl)-3-hexanol | 50 |
| | 750 |

[1)](1S,1'R)-2-[1-(3',3'-dimethyl-1'-cyclohexyl)ethoxy]-2-methylpropyl propanoate; origin: Firmenich SA, Switzerland The addition of 250 parts by weight of 1-[(3E)-2-methyl-3-pentenyl]-cyclopentanol transformed the original perfuming base, which had a simple woody odor, into very natural, balanced fragrance evoking a freshly cut helzelnut wood or hazelnut sap.

What is claimed is:

1. A method to confer, enhance, improve or modify the odor properties of a perfuming composition or of a perfumed article, which method comprises adding to said composition or article an effective amount of at least a compound of formula

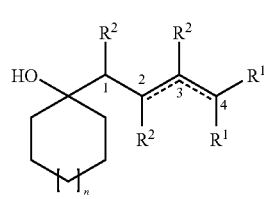

(I)

wherein n represents 0 or 1,
one dotted line between adjacent carbon atoms indicates that a double bond is present while the other dotted line between adjacent carbon atoms represents a single bond;
each $R^1$, independently from each other, represents a hydrogen atom or a methyl or ethyl group; and
at least one $R^2$ group is a methyl or ethyl group and the others are a hydrogen atom or a methyl or ethyl group;
in the form of an isomer of configuration E or Z, or of a mixture thereof, or in an optically active or racemic form.

2. The method according to claim 1, wherein the compound of formula (I) is a compound of formula

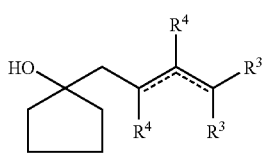

(II)

wherein one dotted line between adjacent carbon atoms indicates that a double bond is present while and the other dotted line between adjacent carbon atoms represents a single bond;
each $R^3$, independently from each other, represents a hydrogen atom or a methyl or ethyl group; and
one $R^4$ group is a methyl or ethyl group and the other $R^4$ group is a hydrogen atom, or a methyl or ethyl group;
in the form of an isomer of configuration E or Z, or of a mixture thereof, or in an optically active or racemic form.

3. The method according to claim 1, wherein the compound of formula (I) is a compound of formula

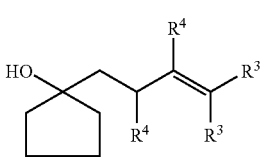

(II')

wherein each $R^3$, independently from each other, represents a hydrogen atom or a methyl or ethyl group; and
one $R^4$ group is a methyl or ethyl group and the other $R^4$ group is a hydrogen atom, or a methyl or ethyl group;
in the form of an isomer of configuration E or Z, or of a mixture thereof, or in an optically active or racemic form.

4. The method according to claim 1, wherein the compound of formula (I) is 1-[2-methyl-3-pentenyl]-cyclopentanol, in the form of an isomer of configuration E or Z or of a mixture thereof.

5. A perfuming ingredient comprising:
i) at least a compound of formula

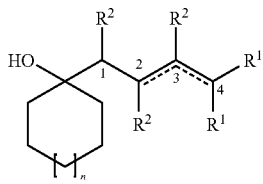

(I)

wherein n represents 0 or 1,
one dotted line between adjacent carbon atoms indicates that a double bond is present while and the other dotted line between adjacent carbon atoms represents a single bond;
each $R^1$, independently from each other, represents a hydrogen atom or a methyl or ethyl group; and
at least one $R^2$ group is a methyl or ethyl group and the others are a hydrogen atom or a methyl or ethyl group;
in the form of an isomer of configuration E or Z, or of a mixture thereof, or in an optically active or racemic form;
ii) at least one ingredient selected from the group consisting of a perfumery carrier and a perfumery base; and
iii) optionally at least one perfumery adjuvant.

6. A perfumed article comprising:
i) at least a compound of formula

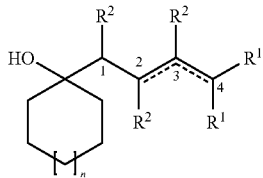

(I)

wherein n represents 0 or 1,
one dotted line between adjacent carbon atoms indicates that a double bond is present while the other dotted line between adjacent carbon atoms represents a single bond;
each $R^1$, independently from each other, represents a hydrogen atom or a methyl or ethyl group; and
at least one $R^2$ group is a methyl or ethyl group and the others are a hydrogen atom or a methyl or ethyl group;
in the form of an isomer of configuration E or Z, or of a mixture thereof, or in an optically active or racemic form; and
ii) a consumer product base.

7. A perfumed article according to claim 6, wherein the consumer product base is a solid or liquid detergent, a fabric softener, a perfume, a cologne or after-shave lotion, a perfumed soap, a shower or bath salt, mousse, oil or gel, a hygiene product, a hair care product, a shampoo, a body-care product, a deodorant or antiperspirant, an air freshener, a cosmetic preparation, a fabric refresher, an ironing water, a paper, a wipe or a bleach.

8. A compound of formula

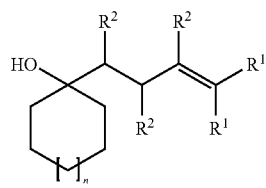

(I')

wherein n is 0;
each $R^1$, independently from each other, represents a hydrogen atom or a methyl or ethyl group; and
at least one $R^2$ group is a methyl or ethyl group and the others are a hydrogen atom or a methyl or ethyl group;
in the form of an isomer of configuration E or Z, or of a mixture thereof, or in an optically active or racemic form.

9. The compound according to claim 8, having the formula

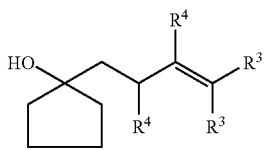

(II')

wherein
each $R^3$, independently from each other, represents a hydrogen atom or a methyl or ethyl group; and
one $R^4$ group is a methyl or ethyl group and the other $R^4$ group is a hydrogen atom or each $R^4$, independently from each other, represents a methyl or ethyl group;
in the form of an isomer of configuration E or Z, or of a mixture thereof, or in an optically active or racemic form.

10. The compound according to claim 8, specifically as 1-[2-methyl-3-pentenyl]-cyclopentanol, in the form of an isomer of configuration E or Z or of a mixture thereof.

* * * * *